United States Patent [19]

Massé et al.

[11] 4,385,520

[45] May 31, 1983

[54] STRAIN AND PHASE DETECTION FOR ROCK MATERIALS UNDER OSCILLATORY LOADING

[75] Inventors: Lucien Massé; William L. Medlin, both of Dallas; James H. Sexton, Duncanville, all of Tex.

[73] Assignee: Mobil Oil Corporation, New York, N.Y.

[21] Appl. No.: 259,774

[22] Filed: May 1, 1981

[51] Int. Cl.[3] ............................................. G01N 29/00
[52] U.S. Cl. ....................................................... 73/579
[58] Field of Search ................. 73/579, 597, 574, 576, 73/573, 808, 811, 789, 794

[56] References Cited

U.S. PATENT DOCUMENTS

| | | | |
|---|---|---|---|
| 1,414,077 | 4/1922 | Fessenden | 73/579 |
| 3,187,565 | 6/1965 | Kreiskorte et al. | 73/579 |
| 3,320,796 | 5/1967 | Darby | 73/576 |
| 3,489,161 | 1/1970 | Rexford | 73/579 |
| 3,589,175 | 6/1971 | Bock et al. | 73/811 |
| 4,058,007 | 11/1977 | Exner | 73/DIG. 1 |

OTHER PUBLICATIONS

"A Review of the Progress in the Measurement of Dynamic Elastic Properties", Hillier, Imperial Chem Industries Ltd., pp. 183–199.
"Effects of Pressure and Fluid Saturation on the Attenuation of Elastic Waves in Sands", Gardner et al., Petroleum Transactions, pp. 189–198, Feb., 1964.
"The Attenuation Constant of Earth Materials", Born, pp. 132–147.

Primary Examiner—Anthony V. Ciarlante
Attorney, Agent, or Firm—C. A. Huggett; M. G. Gilman; G. W. Hager

[57] ABSTRACT

Circumferential and longitudinal strain measurements are carried out on a rock material under oscillatory loading conditions at seismic frequencies. The phase angle between each of these strains and the oscillatory driving force is determined by synchronous and quadrature detection.

2 Claims, 4 Drawing Figures

STRAIN AND PHASE DETECTION FOR ROCK MATERIALS UNDER OSCILLATORY LOADING

BACKGROUND OF THE INVENTION

Many seismic investigation techniques have been developed. For the most part these investigations have been guided by three main sources of data: field seismic records, well logs, and laboratory measurements of ultrasonic pulse velocities in core samples of rock materials. With respect to ultrasonic pulse velocity measurements the travel time of an ultrasonic wavelet is measured between ends of a cylindrical or prismatic bar of rock material. Experimental techniques require a signal wavelet which has died out at the excitation end before it is detected at the receiving end. For samples of practical length this requires a signal frequency of the order of hundreds of kHz. Seismic data are limited to frequencies below a few hundred hertz. Consequently the ultrasonic pulse velocity technique has not permitted measurements at frequencies approaching the seismic range.

SUMMARY OF THE INVENTION

In accordance with the present invention, there is disclosed a mechanical oscillator system having a sample of rock material clamped between a pair of vertically suspended masses, an oscillatory driving force connected to such masses such that the rock material acts as the spring element, detectors of the circumferential and longitudinal strains on the rock material under oscillatory loading, and means for determining the phase angles between the oscillatory driving force and the circumferential and longitudinal strains on the rock material.

DESCRIPTION OF THE PREFERRED EMBODIMENT

The present invention relates to a system for measuring strain amplitude and phase in a rock material under oscillatory loading produced by means of a mechanical oscillator system.

First, the mechanical oscillator system will be described in conjunction with FIGS. 1–2, then the strain and phase detector system will be described in conjunction with FIGS. 3–4.

MECHANICAL OSCILLATOR SYSTEM

Figure 1:
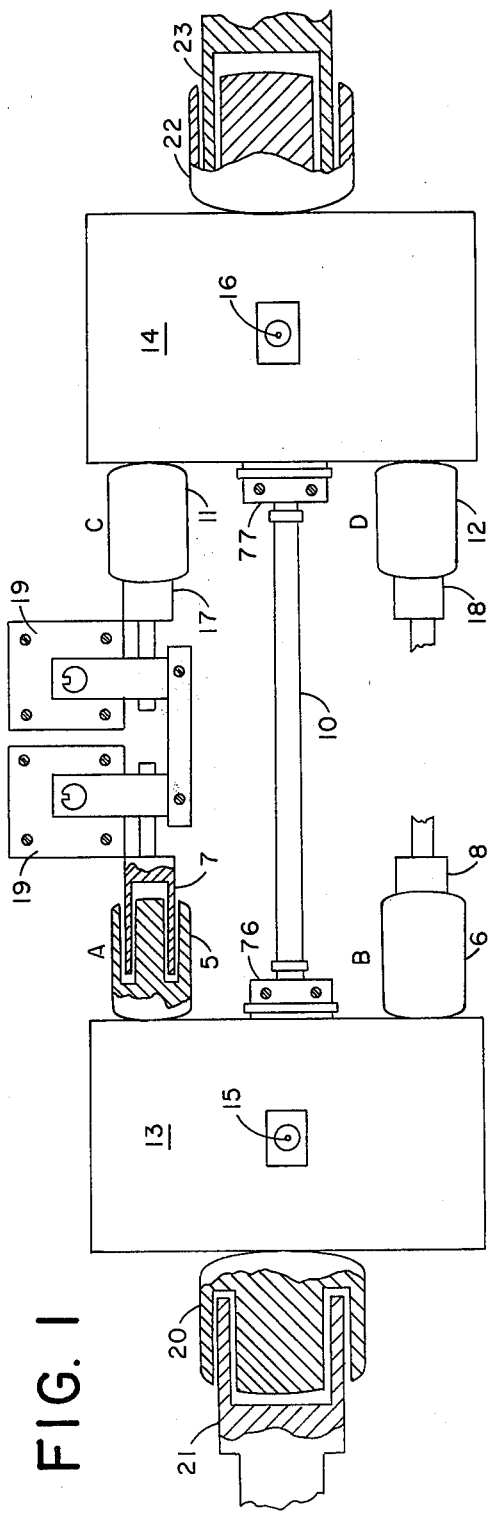
FIG. 1 illustrates a harmonic oscillator system.
Figure 2:
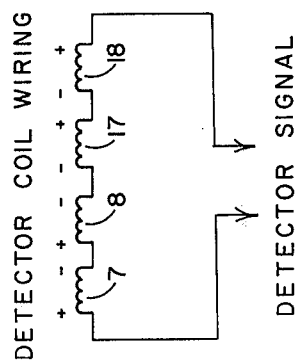
FIG. 2 illustrates a detection system for use in measuring displacements of the masses of the harmonic oscillator of FIG. 1.

Referring now to FIG. 1, the mechanical oscillator utilizes the concept of a mass-spring system with a rock sample acting as the spring. The resonant frequency is determined not only by the dimensions of the rock, which control the spring constant, but by the mass, which can be made very large. By using a large enough mass, resonant frequencies in the seismic range are produced with rock samples of 6 to 10 inches in length. From the resonant frequency the spring constant and Young's modulus of the rock can be determined. An advantage of this method is that it is not necessary to make measurements far below the resonant frequency or to use samples of impractical dimensions to operate in the seismic frequency range. The spring-mass system can also be constructed so as to keep parasitic damping negligibly low. Since the dynamic properties of many rock matrials are amplitude sensitive, it is important that the amplitude of oscillation be kept at or near seismic levels which is also possible by this method.

The rock sample 10 is clamped in a horizontal position between the two masses 13 and 14 which are suspended from a fixed support (not shown) by means of the wires 15 and 16 respectively. For best results the support is seismically isolated from the earth. Mass 13 is attached to a permanent magnet 20 while mass 14 is attached to a permanent magnet 22. Driving coils 21 and 23 are positioned in the air gaps of the magnets 20 and 22, respectively to provide a conventional means for applying driving forces to the masses 13 and 14. A sinusoidal signal of frequency f is applied to each coil with the appropriate polarity to drive the masses in opposition.

The system has two natural modes of vibration, a high frequency one in which the two masses, 13 and 14, move in opposite directions and a lower frequency one in which they move in the same direction. Longitudinal oscillations are produced in the rock sample 10 when the masses move in opposition. This condition is provided when the system is symmetrical, that is, when the masses 13 and 14 are equal, the lengths of wires 15 and 16 are equal, the driving currents to the coils 21 and 22 are equal, and the magnetic field strengths in the air gaps of the magnets are equal. Under such conditions, the low frequency mode is largely eliminated and there is a single prominent resonance.

Resonance measurements require a method for measuring the displacements $X_1$ and $X_2$ of the masses 13 and 14, respectively, or their difference. One method for measuring the relative displacement $|X_1-X_2|$ is illustrated in FIG. 1. A pair of identical permanent magnets 5 and 6 are attached to the mass 13 and a pair of identical permanent magnets 11 and 12 are attached to the mass 14 with their axes lying in a plane perpendicular to the plane of the wire supports, 15 and 16. Identical coils 7, 8, 17 and 18 are positioned in the air gaps of each of the magnets 5, 6, 11 and 12 respectively. These coils are rigidly mounted on the oscillator frame through alignment brackets, 19. Motion of the masses produces an emf in the detector coils. By connecting the coils in series with appropriate polarity as shown in FIG. 2, the signals due to motion of the masses in opposition add and give an emf proportional to $|X_1-X_2|$.

STRAIN AND PHASE ANGLE DETECTOR

Figure 3:
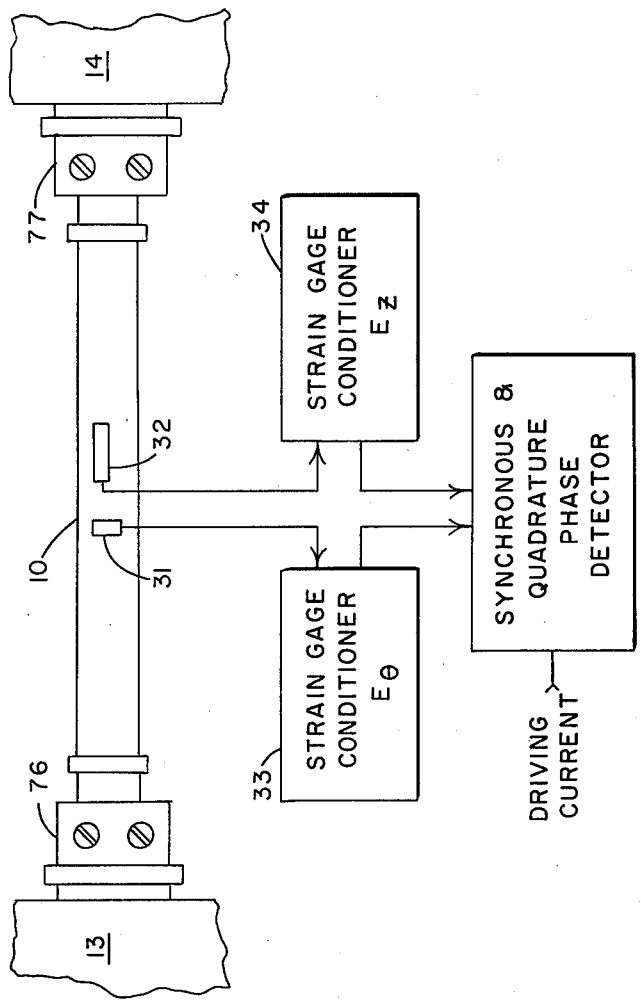
FIGS. 3 and 4 illustrate the strain and phase detector for use with the oscillator system of FIG. 1.
Figure 4:
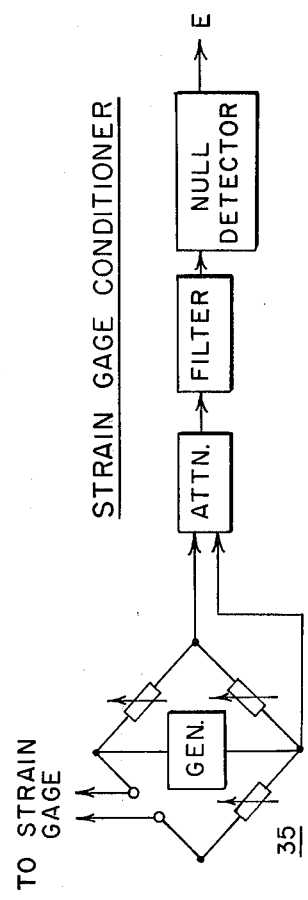

Referring to FIG. 3, the detector 30 is supplied with strain signals $\epsilon_\theta$ and $\epsilon_Z$ representative of the circumferential and longitudinal strains respectively on the rock material while under oscillatory loading. Measurements of such strains are supplied by the bonded circumferential strain gage 31, the bonded longitudinal strain gage 32, and the strain gage conditioning circuits 33 and 34. Each of these conditioning circuits is a bridge-type circuit as illustrated in FIG. 4. The strain gage is coupled as one arm of the typical bridge circuit 35 with its output conditioned by attenuator 36, tuned filter 37 and null detector 38 so as to provide the strain signal.

Also applied to detector 30 is an emf which is exactly in phase with the driving current supplied to the oscillator. This emf is developed across a resistor, having negligible reactance and wired in series with one of the driver coils 21 and 22. Detector 30 is preferably a synchronous and quadrature phase detector system for determining when the circumferential and longitudinal strains $\epsilon_{74}$ and $\epsilon_Z$ respectively, are in-phase or 90° out of phase with the driving current to driver coils 21 and 22 of the oscillator. Such detector systems are commercially available from Ithaco, Inc., Ithaca, N.Y. or from Princeton Applied Research, Princeton, N.J.

While the strains and phase detection system of the present invention for use with a mechanical oscillator has been shown and described, additional modifications are within the spirit and scope of the invention. The appended claims are intended to cover all such modifications.

What is claimed is:

1. In a system for measuring resonance characteristics of rock material under an oscillatory driving force, the improvement comprising:
   (a) means for producing an emf which is exactly in phase with said oscillatory driving force,
   (b) means for producing a signal proportional to the longitudinal strain on said rock material under oscillatory loading,
   (c) means for producing a signal proportional to the circumferential strain on said rock material under oscillatory loading, and
   (d) means for determining the phase angles between said emf and said strain signals.
2. The system of claim 1 wherein said driving force is provided by a coil magnet system driven with a sinusoidal current, whereby said driving force is in phase with said driving current.

* * * * *